United States Patent
Kulkarni et al.

(10) Patent No.: US 11,345,939 B2
(45) Date of Patent: May 31, 2022

(54) PREPARATION OF EPA AND DHA ENRICHED GLYCERIDES

(71) Applicant: PRAJ INDUSTRIES LIMITED, Pune (IN)

(72) Inventors: Mangesh Ganesh Kulkarni, Hinjewadi (IN); Prajakt Subhash Charhate, Hinjewadi (IN); Pramod Ramchandra Patil, Hinjewadi (IN)

(73) Assignee: PRAJ INDUSTRIES LIMITED, Pune (IN)

( * ) Notice: Subject to any disclaimer, the term of this patent is extended or adjusted under 35 U.S.C. 154(b) by 0 days.

(21) Appl. No.: 16/641,062

(22) PCT Filed: Aug. 21, 2018

(86) PCT No.: PCT/IN2018/050538
§ 371 (c)(1),
(2) Date: Feb. 21, 2020

(87) PCT Pub. No.: WO2019/038783
PCT Pub. Date: Feb. 28, 2019

(65) Prior Publication Data
US 2020/0370079 A1    Nov. 26, 2020

(30) Foreign Application Priority Data

Aug. 22, 2017    (IN) .............................. 201721029626

(51) Int. Cl.
*C12N 9/20* (2006.01)
*C12P 7/6472* (2022.01)

(52) U.S. Cl.
CPC .............. *C12P 7/6472* (2013.01); *C12N 9/20* (2013.01)

(58) Field of Classification Search
CPC ................................. C12N 9/20; C12P 7/6472
See application file for complete search history.

(56) References Cited

FOREIGN PATENT DOCUMENTS

| EP | 1575374 | * | 6/2004 |
| WO | 2009/040676 | * | 4/2009 |
| WO | 2012087153 A1 | | 6/2012 |

OTHER PUBLICATIONS

A. Olivares et al. "Enzyme assisted fractionation of wood sterols mixture by short path distillation", Chemical Engineering Journal 191:55 (Year: 2012).*
W. Klaypradit et al. "Characterization of Refined Oils from Atlantic Salmon Belly as Affected by Degumming", Kasetsart University Fisheries Research Bulletin 38(3):1-15 (Year: 2014).*
International Search Report and Written Opinion, dated Dec. 27, 2018.

* cited by examiner

*Primary Examiner* — Tekchand Saidha
(74) *Attorney, Agent, or Firm* — Billion & Armitage

(57) ABSTRACT

The invention relates to a process for the preparation of EPA and DHA enriched glycerides from degummed oil using microbial lipase enzymes. It particularly relates to the use of very less concentrations of said enzymes and water for the hydrolysis process. Used lipase enzymes specifically removes non-EPA/DHA fatty acids which results in enriched and balanced content of EPA/DHA in to the final product.

14 Claims, No Drawings

PREPARATION OF EPA AND DHA ENRICHED GLYCERIDES

FIELD OF THE INVENTION

The invention relates to a process for the preparation of EPA and DHA enriched glycerides from degummed oil using microbial lipase enzymes. It particularly relates to the use of very less concentrations of said enzymes and water for the hydrolysis process. Used lipase enzymes specifically removes non-EPA/DHA fatty acids which results in enriched and balanced content of EPA/DHA in to the final product.

BACKGROUND

Eicosapentaenoic acid (EPA) and docosahexaenoic acid (DHA) are members of omega-3 fatty acids (PUFA). It has been established that the omega-3 fatty acids reduce inflammation, helping to prevent inflammatory diseases like heart diseases and arthritis. They are also essential for the development of brain, affecting the behaviour and cognitive functions, and are especially necessary during fetal development in humans. EPA is used to control for high blood pressure in high-risk pregnancies, schizophrenia, personality disorder, cystic fibrosis, Alzheimer's disease, depression and diabetes. DHA is used for treating type-2 diabetes, coronary artery disease, dementia, and attention deficit-hyperactivity disorder. DHA is also used for improving vision, preventing an eye disease called age-related macular degeneration, preventing and treating depression, and reducing aggressive behaviour in people in stressful situations. EPA and DHA present in fish oil preparations are used for a variety of conditions like asthma, cancer, menstrual problems, hot flashes, hay fever, lung diseases, lupus erythematosus, and kidney disease. EPA and DHA are also used in combination for migraine headache prevention in adolescents, skin infections, Behçet's syndrome, high cholesterol, high blood pressure, psoriasis, Raynaud's syndrome, rheumatoid arthritis, Crohn's disease, and ulcerative colitis. Generally, EPA and DHA are used in its ethyl ester form for nutraceutical uses. But physiologically triglycerides of EPA and DHA are better absorbed when taken orally compared with ethyl esters of EPA and DHA leading to effective metabolic utilization of it. Common sources of EPA and DHA fatty acids include fish oil, algal oil, egg oil, squid oils, krill oil, etc. In general products containing with 60% EPA/DHA [38% EPA to 22% DHA], 50% total EPA/DHA [30% EPA to 20% DHA] and 30% EPA/DHA [18% EPA to 12% DHA] are in demand in the market but oils obtained from a variety of fishes have a lower EPA and DHA concentration.

The available methods to increase the concentration of omega-3 polyunsaturated fatty acids (PUFA) are adsorption chromatography, fractional or molecular distillation, enzymatic splitting, low-temperature crystallization, supercritical fluid extraction and urea complexation etc. Very few of them are suitable for large-scale processes.

Enzymatic processes for concentrating omega-3 fatty acids are well known in the prior art. They are as more environmentally friendly compared to chemical processes. Since these fatty acids are highly sensitive to oxidation, enzymatic methods allow the application of mild reaction conditions, at lower temperature and pressure, which is important when dealing with omega-3 fatty acids. Low temperature also improves the feasibility of the process. Lipase-catalysed hydrolysis is one of the most widely used enzymatic reactions, for the purpose of improvement of the omega-3 concentration of fish oil.

Lipases can catalyze both hydrolysis and esterification reaction of oils with a reasonable rate, depending upon their origin from microbes such as *Candida rugosa*, *Candida antarctica*, *Pseudomonas*, *Mucor miehei*, *Rhiopus oryzae* etc. Hydrolysis with lipases can be carried out both selectively and non-selectively depending upon the nature and the overall shape of the acyl-chain binding active site in lipases. For the synthesis of EPA-DHA rich glycerides, lipase catalyzed hydrolysis of oil is reported as the first step to release free unwanted fatty acids from the breakdown of ester bonds of triglycerides in fish oil. The enzymatic process is commonly followed by a separation process such as membrane filtration or molecular distillation whereby the hydrolyzed free fatty acids are removed and oil is obtained with an increased/enriched content of omega-3 fatty acids.

Although lipase catalysed process are recognized in the prior art, there is need of cost effective, simple, industrial scale method with balanced content of EPA-DHA for economic commercialisation of the EPA/DHA enriched products. Herein process of the preparation of EPA and DHA enriched glycerides is disclosed having advantages over known methods. It is industrially scalable, economic and safe with balanced content of EPA-DHA in the final products.

DETAIL DESCRIPTION

In one embodiment of the invention, the process comprises crude degummed fish oil consisting EPA and DHA in glyceride form or any other source rich in EPA or DHA omega-3 fatty acids; mixing said oil with water to form a reaction mixture; heating said mixture at desired temperature with continuous stirring; contacting said reaction mixture with lipase for desired time; separating fraction of water from said mixture to form a first stream; evaporating said first stream to remove remaining water to form a second stream; subjecting said second stream to molecular distillation at desired conditions to separate free fatty acid as a distillate forming a residual stream; and finally collecting said residual stream having said enriched glycerides. The process affording about 80% recovery of EPA and DHA in final product.

Fish oil contains phospholipids which are phosphorus containing triglycerides. Normally enzymes are very sensitive phosphorus and can lost their activity in presence of high amount of phosphorus. In order to avoid this oil is normally degummed using water and phosphoric acid.

Present invention facilitates efficient preparation of EPA and DHA enriched glycerides from degummed fish oil by process comprising four steps namely: 1] preparation of reaction mixture, 2] hydrolysis of reaction mixture 3] washing of reaction mixture, and 4] molecular distillation. Each step has one or more elements for performing specific or optional functions as required for achieving selective preparation of glycerides of EPA and DHA. A person skilled in the art may appreciate different variation and/or combination of these elements that may be used to perform the object of the invention disclosed herein.

Step 1: Preparation of Reaction Mixture

Degummed sardine fish oil containing EPA and DHA is taken as a feed stock. To prepare EPA and DHA enriched glycerides, said oil is mixed with equal quantity of processing water and heated to about 55° C. with continuous stirring. Said formed reaction mixture is further used for enzymatic hydrolysis. In yet another embodiment of the invention, the oil is mixed with water in ratio of about 1:0.5 to about 1:1 (w/w). In yet another embodiment of the invention, oil is obtained from one or more fish species selected from one or more of sardine, tuna, anchovy or similar fishes.

Step 2: Hydrolysis of Reaction Mixture

Said reaction mixture is used further for enzymatic hydrolysis using microbial lipase enzyme[s]. Said hydrolysis is carried out at about 55° C. under about 1-kg of nitrogen pressure for about 10 to about 24 hours at agitation of about 280 RPM. On completion of reaction, reaction mass is heated to about 90° C. to deactivate the lipases. Said microbial lipases are obtained from one or more of *Candida antarctica, Rhizomucor miehei, Thermomyces anuginoss, Candida rugosa* or *Rhizopus oryzae* in a concentration of about 0.75% to about 1.5% by weight of oil. Herein, the lipase catalysed hydrolysis is a major step in concentration of EPA-DHA as it releases free fatty acids other than EPA-DHA by breaking down the ester bonds of triglycerides in fish oil.

Most preferably, lipase of *Candida antarctica* is used for EPA-DHA enrichment in a concentration of about 1% by weight based on the amount of oil. *Candida antarctica* lipase is a selective lipase for long chain fatty acids because it has a very narrow and deep substrate binding site in comparison to other lipases. This small space inside the binding site causes to allow only very specific substrate to bind with it and hence result into high degree of selectivity for non-EPA/DHA fatty acids removal from the triglycerides helping achieve higher concentrations of about 18% of EPA and 12% of DHA in treated products. In another embodiment of present invention, enzyme hydrolysis is carried out in two steps with using two different lipases having different characteristics. In certain embodiment of the invention, a surfactant is added to increase the efficiency and final yield of product.

Step 3: Washing of Reaction Mixture

After deactivation of enzymes, said reaction mixture is settled further for about 30 minute to felicitate the aqueous and organic layer separation. Water layer is separated at the bottom of the reactor form said first stream. Said first stream is then washed further with water to remove remaining enzymes completely. Next, said washed organic layer is dried in evaporator or in dryer between about 80° C. and about 100° C. to form a second stream.

Step 4: Molecular Distillation of Second Stream

To purify the glycerides of EPA and DHA, the second stream obtained in third step are subjected to molecular distillation at desired temperature, vacuum and agitations. This step leads to two fractions; the residue stream contained about 45% of glyceride enriched with EPA/DHA by weight and distillate stream contained mainly free fatty acids along with small fraction of EPA and DHA. Said residual stream comprises about 14% to about 18% of EPA by weight and about 8% to about 13% of DHA by weight. Said glycerides enrichment process afforded up to 80% recovery of EPA and DHA in the final product. Said residue stream having final product is useful as an ingredient in food and nutraceutical products.

Advantages of the Disclosed Process are:
  The disclosed process is used to selectively remove non-EPA/DHA fatty acid and enrich EPA and DHA glycerides.
  The disclosed process is not only enriches the EPA-DHA content but also provides a balanced amount of it in the final product.
  The disclosed process uses substantially less concentration of water and enzymes in processing.
  Disclosed process provides about 14% to about 18% of EPA by weight and about 8% to about 13% of DHA by weight in the final product.
  The recovery of EPA/DHA in glyceride forms is up to 80% of total amount.
  The disclosed process is substantially more economical and with a minimum processing steps.

Examples provided below give wider utility of the invention without any limitations as to the variations that may be appreciated by the person skilled in the art. A non-limiting summary of various experimental results is given in the examples, which demonstrate the advantageous and novel aspects of the process for the preparation of EPA and DHA enriched glycerides from degummed fish oil using microbial lipase enzyme.

Example 1

About 40 kg of refined fish oil [containing about 12.14% EPA, about 7.63% DHA] and 40 litres of process water was mixed and heated for about 55° C. with continuous stirring. Said mixture was used further for enzymatic hydrolysis using about 600 g of lipase enzyme from *Candida antarctica*. Said hydrolysis was carried out at about 55° C. under 1-kg of nitrogen pressure for about 24 hours at agitation of about 280 RPM. After the reaction was completed said reaction mass was heated to about 90° C. to deactivate the enzymes and settled further for about 30 minute to facilitate the aqueous and organic layers separation. Water layer was separated from the bottom of the reactor. And said organic layer was washed (using 20 litres water) to remove remaining enzymes completely. Said washed organic layer was dried further at about 100° C. This process conferred about 38.2 kg of hydrolysed oil. Next, said hydrolysed oil was subjected to molecular distillation step for the removal of fatty acids at temperature of about 210° C. under vacuum of about 0.01 mmHg, at a flow rate about 20 kg/h and at agitation of about 280 RPM. This step afforded about 18.83 kg of residue stream and about 16.73 kg of distillate stream. Said residue stream having about 18.26% EPA, and about 12.67% DHA in the form of glycerides and said distillate stream containing mainly free fatty acids with about 4.28% EPA, and about 1.94% DHA.

Example 2

About 40 kg of crude fish oil [containing about 13.84% EPA, about 9.64% DHA] and 40 litres of process water was mixed and heated it for about 55° C. with continuous stirring. Said mixture was used further for enzymatic hydrolysis using about 400 g of lipase enzyme from *Candida antarctica*. Said hydrolysis was carried out at about 55° C. under 1-kg of nitrogen pressure for about 4 hours at agitation of about 280 RPM. After the reaction was completed said reaction mass was heated to about 90° C. to deactivate the enzyme and settled further for about 30 minute to facilitate the aqueous and organic layers separation. Water layer was separated from the bottom of the reactor. And said organic layer was washed (using 20 litres water) to remove remaining enzymes completely. Said washed organic layer was dried further at about 100° C. This process conferred about 37.8 kg of hydrolysed oil.

Next, said hydrolysed oil was subjected to molecular distillation step for the removal of fatty acids at temperature of about 200° C. under vacuum of about 0.01 mmHg at a flow rate about 20 kg/h and at agitation of about 280 RPM. This step afforded about 22.75 kg of residue stream and about 13.83 Kg of distillate stream. Said residue stream having about 19.4% EPA, and about 14.03% DHA in the form of glycerides and said distillate stream contains mainly free fatty acids with about 3.53% EPA, and about 2.24% DHA.

Example 3: Selection of Suitable Lipase for Hydrolysis Reaction

About 100 g of crude or refined oil was mixed with 100 g of water. and heated it for about 55° C. with continuous stirring. Said mixture was used further for enzymatic hydrolysis using about 1 g of different lipase enzymes from different microorganisms Said hydrolysis was carried out at about 55° C. for up to 24 hours at agitation of about 280 RPM. After the reaction was completed said reaction mass was heated to about 90° C. to deactivate the enzymes and settled further for about 30 minute to facilitate the aqueous and organic layers separation. Water layer was separated from the bottom of the reactor. And said organic layer was washed to remove enzymes completely. Said washed organic layer was dried further at about 100° C. Next, said hydrolysed oil was subjected to molecular distillation step for the removal of fatty acids at temperature of about 180-210° C. under vacuum of about 0.01 mmHg. Table 2 shows different enzymes used for the preparation of glycerides of EPA and DHA as method disclosed herein. Of different enzymes used only *Candida antarctica* (crude and refined) provided balanced content of EPA/DHA in final product.

Example 4

Process of Example 3 was repeated with refined oil with same experimental condition and enzyme concentration, but with different enzyme hydrolysis time. Results are shown in Table 3.

TABLE 2

| Lipase from: | Type of Oil | Initial concentration in Feed | | Glyceride Fraction | | | Non Glyceride Fraction |
|---|---|---|---|---|---|---|---|
| | | EPA [%] | DHA [%] | EPA [%] | DHA [%] | Yield [%] | Yield [%] |
| *Candida antarctica* | Crude | 11.95 | 7.43 | 17.64 | 11.96 | 41.48 | 52.9 |
| *Candida rugosa* | Crude | 11.4 | 12.42 | 11.37 | 23.01 | 36.8 | 62.00 |
| *Rhizomucor miehei* | Crude | 11.95 | 7.43 | 11.97 | 8.64 | 57.06 | 34.12 |
| *Thermomyces lanuginosa* | Crude | 11.95 | 7.43 | 7.58 | 9.89 | 35.29 | 56.35 |
| *Rhizopus oryzae* | Crude | 11.4 | 12.42 | 10.07 | 18.77 | 40.08 | 57.14 |
| *Candida antarctica* | Refined | 12.39 | 7.65 | 15.57 | 10.56 | 63.75 | 34.97 |
| *Thermomyces lanuginosa* | Refined | 12.39 | 7.65 | 11.5 | 7.47 | 96.02 | 3.88 |
| *Candida rugosa* | Refined | 12.39 | 7.65 | 12.01 | 16.25 | 34 | 62 |

TABLE 3

| Enzyme | Hydrolysis time [H] | Initial concentration in Feed | | Glyceride Fraction | | | Non Glyceride Fraction |
|---|---|---|---|---|---|---|---|
| | | EPA [%] | DHA [%] | EPA [%] | DHA [%] | Yield [%] | Yield [%] |
| *Candida antarctica* | 10 | 13.89 | 6.55 | 18.07 | 8.87 | 57.62 | 38.51 |
| *Candida antarctica* | 24 | 12.39 | 7.65 | 15.57 | 10.56 | 63.75 | 34.97 |
| *Candida antarctica* | 36 | 13.89 | 6.55 | 14.48 | 9.78 | 60.3 | 38.3 |
| *Candida antarctica* | 48 | 13.89 | 6.55 | 14.14 | 9.63 | 53.56 | 42.74 |

Example 6

Process of Example 3 was repeated with crude oil with same experimental condition but varying the concentrations of enzyme from *Candida antarctica*. Results are shown in Table 4. The 1% enzyme concentration shows best enrichment results.

Example 7

To check the effect of water concentration, Process of Example 3 was repeated with crude oil with same experimental condition but varying the ratio of oil to water. Results are shown in Table 5.

TABLE 4

| Exp. No. | Reaction parameters Time [H] | Reaction parameters Enz. Conc. [%] | Initial concentration in Feed EPA [%] | Initial concentration in Feed DHA [%] | Glyceride Fraction EPA [%] | Glyceride Fraction DHA [%] | Yield [%] | Non Glyceride Fraction Yield [%] |
|---|---|---|---|---|---|---|---|---|
| 1 | 4 | 0.50 | 14.53 | 10.73 | 17.7 | 13.29 | 65.00 | 32.43 |
| 2 | 4 | 0.75 | 13.84 | 9.64 | 19.13 | 13.59 | 62.82 | 36.62 |
| 3 | 4 | 1.00 | 14.52 | 10.69 | 19.5 | 14.2 | 62.98 | 35.83 |

TABLE 5

| Oil to Water Ratio | Type of Oil | Enzyme Conc. [%] | Initial concentration in Feed EPA [%] | Initial concentration in Feed DHA [%] | Glyceride Fraction EPA [%] | Glyceride Fraction DHA [%] | Yield [%] | Non Glyceride Fraction Yield [%] |
|---|---|---|---|---|---|---|---|---|
| 1:1 | Crude | 1 | 13.84 | 9.64 | 21.3 | 15.72 | 43.88 | 53.06 |
| 1:0.5 | Crude | 1 | 13.84 | 9.64 | 20.3 | 14.96 | 36.54 | 62.5 |

We claim:

1. An industrially scalable process for preparation of eicosapentaenoic acid (EPA) and docosahexaenoic acid (DHA) enriched glycerides from crude degummed fish oil consisting essentially of:
   a) mixing crude degummed fish oil with water forming a reaction mixture;
   b) heating said reaction mixture at desired temperature with continuous stirring;
   c) contacting said reaction mixture with lipase for desired time;
   d) separating fraction of water from said reaction mixture forming a first stream;
   e) evaporating said first stream to remove remaining water forming a second stream;
   f) subjecting said second stream to molecular distillation at desired conditions to separate free fatty acid as a distillate forming a residual stream; and
   g) collecting said residual stream, wherein said residual stream comprises EPA and DHA enriched glycerides.

2. The process of claim 1, wherein said reaction mixture comprises the crude degummed fish oil and water in a mass ratio of about 1:1.

3. The process of claim 1, wherein said lipase is microbial lipase obtained from one or more of *Candida antarctica, Rhizomucor miehei, Thermomyces lanuginosa, Candida rugosa* or *Rhizopus oryzae*.

4. The process of claim 1, wherein said heating is performed at about 55° C. for about 16 to about 24 hours.

5. The process of claim 1, wherein said lipase concentration is about 0.75 to about 1.5% by weight of the crude degummed fish oil.

6. The process of claim 1, wherein said evaporation is performed between about 80° C. to about 100° C.

7. An industrially scalable process for preparation of EPA and DHA enriched glycerides from crude degummed fish oil consisting essentially of:
   a) mixing crude degummed fish oil with water forming a reaction mixture in a reactor, wherein said reaction mixture comprises the crude degummed fish oil and water in a mass ratio of about 1:1;
   b) heating said reaction mixture to about 55° C. for about 16 to about 24 hours with continuous stirring;
   c) contacting said reaction mixture with lipase obtained from *Candida antarctica* for up to 24 hours, wherein said lipase concentration is about 0.75 to about 1.5% by weight of the crude degummed fish oil, and then deactivating the lipase after the hydrolysis reaction is complete by heating said reaction mixture to 90° C.;
   d) allowing a water layer and an organic layer to form in the reactor and separating the water layer from the bottom of the reactor, said organic layer forming a first stream;
   e) evaporating said first stream to remove remaining water forming a second stream;
   f) subjecting said second stream to molecular distillation at desired conditions to separate free fatty acid as a distillate forming a residual stream; and
   g) collecting said residual stream having said EPA DHA enriched glycerides; wherein said molecular distillation is performed at temperature between about 160° C. to about 210° C. in vacuum between about 0.03 to about 0.05 mTorr and agitation rate of about 280 RPM.

8. The process of claim 1, wherein said residual stream comprises about 14 to about 18% of EPA by weight.

9. The process of claim 1, wherein said residual stream comprises about 8 to about 13% of DHA by weight.

10. An industrially scalable process for preparation of EPA and DHA enriched glycerides from crude degummed fish oil comprising:
    a) mixing crude degummed fish oil with water forming a reaction mixture;
    b) heating said reaction mixture at desired temperature with continuous stirring;
    c) contacting said reaction mixture with lipase for desired time;
    d) separating fraction of water from said reaction mixture forming a first stream;
    e) evaporating said first stream to remove remaining water forming a second stream;
    f) subjecting said second stream to molecular distillation at desired conditions to separate free fatty acid as a distillate forming a residual stream; and
    g) collecting said residual stream, wherein said residual stream comprises EPA DHA enriched glycerides, wherein contacting said reaction mixture with lipase for desired time comprises a first hydrolysis step with a first lipase followed by a second hydrolysis step with a second lipase, wherein the first lipase and the second lipase are different.

11. The process of claim 1, wherein contacting said reaction mixture with lipase further comprises adding a surfactant.

12. The process of claim 1, further comprising deactivating the lipase by heating said reaction mixture to 90° C. before separating said water fraction.

13. The process of claim 1, wherein said reaction mixture comprises the crude degummed fish oil and water in a mass ratio of about 1:1, said lipase concentration is about 1% by weight of the crude degummed fish oil, and said lipase is obtained from *Candida antarctica*.

14. The process of claim 7, wherein the crude degummed fish oil is obtained from sardine, tuna, or anchovy.

* * * * *